United States Patent [19]

Peek

[11] 3,993,047

[45] Nov. 23, 1976

[54] INSTRUMENTATION FOR MONITORING BLOOD CIRCULATION

[76] Inventor: Sanford C. Peek, 111 Summer St., Hingham, Mass. 02043

[22] Filed: Oct. 8, 1975

[21] Appl. No.: 620,701

Related U.S. Application Data

[63] Continuation-in-part of Ser. No. 487,150, July 10, 1974, abandoned.

[52] U.S. Cl. .................... 128/2.05 P; 128/2.05 T; 128/2.05 V
[51] Int. Cl.² .......................................... A61B 5/02
[58] Field of Search ................ 128/2.05 T, 2.05 P, 128/2.05 V, 2.06 A, 2.06 F, 2 L

[56] References Cited
UNITED STATES PATENTS

| | | | |
|---|---|---|---|
| 2,640,389 | 6/1953 | Liston | 128/2 L |
| 3,139,086 | 6/1964 | Botsch et al. | 128/2.05 T |
| 3,228,391 | 1/1966 | Fitter et al. | 128/2.05 T |
| 3,426,747 | 2/1969 | Herman et al. | 128/2.05 T |
| 3,575,162 | 4/1971 | Gaarder | 128/2.05 T |
| 3,628,525 | 12/1971 | Polanyi | 128/2.05 P |
| 3,672,353 | 6/1972 | Crovella et al. | 128/2.06 A |
| 3,742,937 | 7/1973 | Manuel et al. | 128/2.05 T |
| 3,835,837 | 9/1974 | Peek | 128/2.05 P |
| 3,841,314 | 10/1974 | Page | 128/2.05 T |
| 3,881,481 | 5/1975 | Heule et al. | 128/2.05 V |

*Primary Examiner*—Kyle L. Howell

[57] ABSTRACT

Compact monitor apparatus for monitoring a blood circulation condition comprises a radiation source and a radiation sensor mounted in spaced, side by side relation. The source and sensor are placed in contact with the skin and the pulsating blood flow immediately beneath the skin significantly changes the transmission of radiation as a function of the amount of blood flow in that region. Filter circuitry is connected to the sensor and tuned to attenuate artifact signals and enhance the pulsating blood signals. An output indicator responds to the enhanced pulsating blood signals to produce an indication of the monitored blood circulation condition.

18 Claims, 7 Drawing Figures

U.S. Patent  Nov. 23, 1976  3,993,047
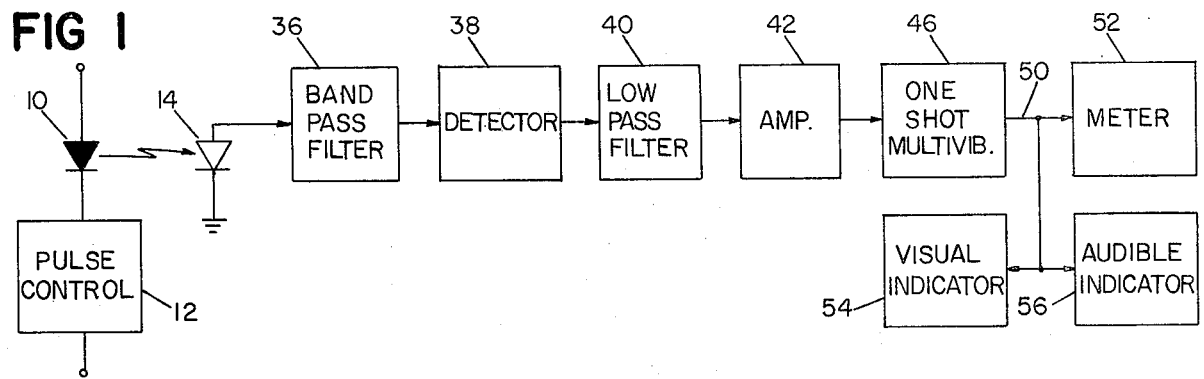
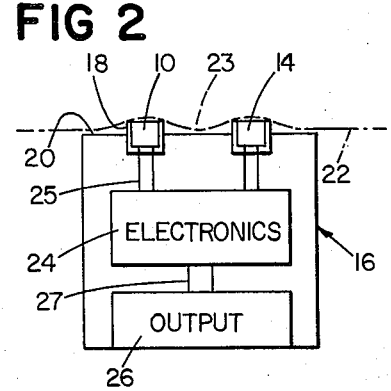
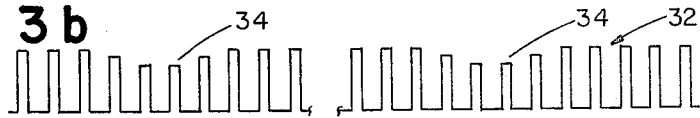
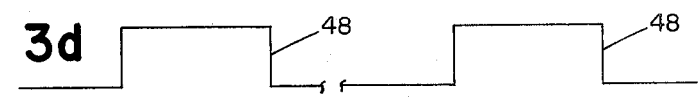
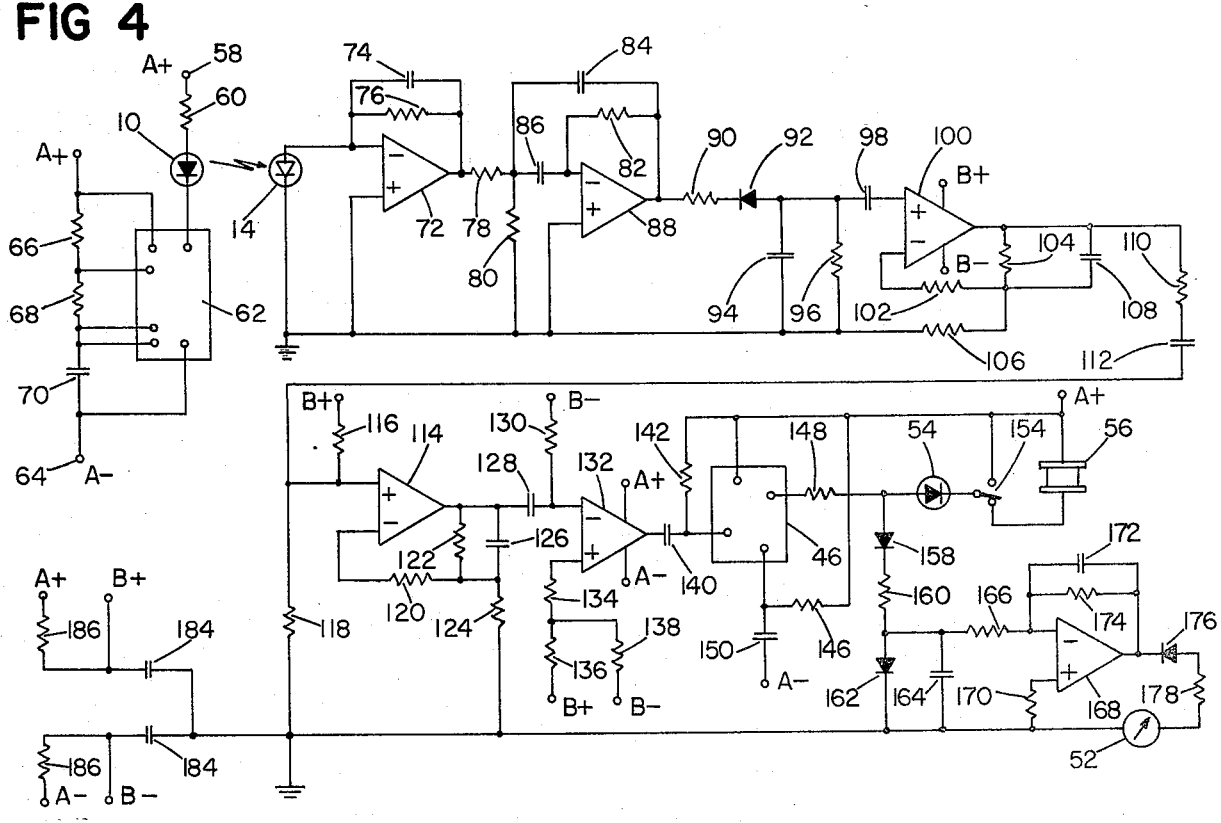

INSTRUMENTATION FOR MONITORING BLOOD CIRCULATION

This application is a continuation-in-part of my copending patent application Ser. No. 487,150, filed July 10, 1974 entitled "Pulse Monitor" now abandoned.

SUMMARY OF INVENTION

This invention relates to medical instrumentation and more particularly to instrumentation for monitoring blood circulation.

Numerous methods and apparatus have been suggested for monitoring blood circulation. Examples of such apparatus include electrocardiographs and comparatively elaborate instrumentation that employs sensors inserted into the bloodstream. In addition, numerous pulse rate monitors have been suggested such as are described in Botsch et al. U.S. Pat. No. 3,139,086, Herman et al. U.S. Pat. No. 3,426,747, and Peek U.S. Pat. No. 3,835,837. There exists, however, a need for an improved instrument which would provide a sensitive indication of circulation conditions of persons such as patients in hospitals with potential circulation deficiencies or impairments and in turn a warning of incipient or potential difficulty. There are many circumstances where a small, portable, inexpensive, easy to use instrument which would provide a continuing indication of the patient's current blood circulation condition would be desirable. A particular need exists for an instrument capable of monitoring blood circulation conditions of patients at locations on the body such as extremities where the pulse may be difficult to discern or when the pulse is weak, and where existing elaborate instrumentation is difficult to apply. Accordingly, it is an object of this invention to provide a novel and improved blood circulation monitoring instrument which provides an output indication of pulse rate as an indication of blood circulation.

In accordance with the invention there is provided a compact monitor unit which includes a radiation source which has an output in the infrared region and an infrared sensor in side by side relation and arranged to be disposed so that the source and sensor are not directly exposed to each other but will be exposed to adjacent skin surface areas of the patient or user. Preferably the source and sensor elements protrude above the adjacent surface of the unit so that in use flesh is interposed between the source and sensor and the radiation sensed by the sensor has penetrated deeper into the flesh where there is a greater quantity of blood than is the case where the source and sensor elements are flush with or recessed into the surface of the unit. In a preferred embodiment an oscillator energizes the radiation source to generate radiation pulses in the infrared region at a relatively high frequency rate and the photosensor senses infrared radiation pulses emanating from that portion of the patient's body to which the photosensor is directly exposed. The pulsating blood flow immediately beneath the skin surface significantly changes the transmission of radiation pulses in the infrared region as a function of the amount of blood in that region and thus imposes a modulation of the amplitude of the emanated infrared pulse signals. Artifact signals are removed from the resulting signals by band pass circuitry that is connected to the infrared sensor and is tuned to pass signals of frequency corresponding to the oscillator frequency and to block lower frequency and higher frequency signals. Thus blood pulsing information is transmitted in terms of modulation of signals at the oscillator frequency (e.g. 2 Kilohertz) and artifact signals at other frequencies are blocked. Detector circuitry connected to the band pass circuitry responds to the modulation and produces a series of output pulses corresponding in repetition rate to the blood pulse rate (e.g. 1–3 Hertz). Further artifact signal removal is accomplished by low pass circuitry connected to the detector circuitry which is tuned to pass only signals at a frequency substantially less than the power distribution frequency (e.g. 60 Hertz). The resulting blood pulse signal from the low pass circuitry is then shaped and applied as a triggering pulse to a one-shot pulse generator to generate another pulse of predetermined amplitude and duration. Thus, by signal processing techniques artifact signals from a variety of potential sources external to the blood circulation system are excluded and a well-defined triggering signal corresponding to each sensed systolic blood pressure transition is generated to trigger the one-shot pulse generator. According to another feature of the invention the repetition rate of the pulse generator is limited to a maximum rate of about three pulses per second and thus provides further specific discrimination against artifact signals. The resulting output may be displayed (either locally or at a remote location) and/or recorded for convenient monitoring of the patient's blood circulation at the particular body location of interest. Supplemental visual and/or audible pulse indications are also conveniently available if desired. In a particular embodiment the resulting series of pulses are integrated to generate a signal level that provides an accurate indication of the patient's or user's pulse rate.

The invention provides a sensitive and accurate blood circulation monitor device that is inexpensive, unobtrusive and convenient to use and that is effective to monitor blood circulation conditions at body locations that have heretofore been difficult or impossible to effectively monitor. Other objects, features and advantages of the invention will be seen as the following description of a particular embodiment progresses, in conjunction with the drawing, in which:

FIG. 1 is a block diagram of a system constructed in accordance with the invention;

FIG. 2 is a schematic diagram indicating a sensor configuration employed in the embodiment shown in FIG. 1;

FIGS. 3a-3d are a series of timing diagrams of signals generated in the circuit shown in FIG. 1; and FIG. 4 is a schematic diagram of circuitry incorporated in the embodiment shown in FIG. 1.

DESCRIPTION OF PARTICULAR EMBODIMENT

The system shown in FIG. 1 includes an infrared radiation source 10 that is connected to a pulse control 12 which in this embodiment is a multivibrator that gates source 10 on at a two Kilohertz rate and a 20% duty cycle thus producing a series of infrared radiation pulses. An infrared sensor 14 is disposed in side by side relation to source 10. As indicated in FIG. 2, source 10 and sensor 14 are mounted in housing 16. Suitable shield structure, such as casings 18, is disposed between source 10 and sensor 14 and prevents output radiation of source 10 from being sensed directly by sensor 14. The photosensor 14 should be spaced at least 0.1 inch on center from the infrared radiation source 10 in order to provide sufficient distance for the interposed blood to influence the sensed infrared radiation. The spacing is preferably about 0.25 inch but may be substantially greater including values up to about 1 inch. Increase in the sensor-source spacing generally provides some improvement in the signal to noise ratio but usually with concurrent reduction in signal magnitude. It has been also found that improved output signal enhancement is obtained when source 10 and sensor 14 protrude slightly above surface 20 of housing 16—protrusion in the range of 0.05–0.1 inch providing satisfactory results. Surface 20 of housing 16 is designed to be placed in contact with the skin surface 22 of the patient at the location where it is desired to monitor the pulse of the patient. When the monitor is so secured, the patient's skin bulges downwardly into the space between protruding source 10 and sensor 14 as indicated at 23 in FIG. 2 and thus interposes a deeper portion of flesh in that region 23 and in the path through which infrared radiation from source 10 passes for sensing by sensor 14 so that the radiation penetrates deeper into the flesh where greater amounts of blood are present. Source 10 and sensor 14 may be used in a unit integral with and connected to electronics 24 by conductors 25 which in turn is connected to output indicator 26 by conductor 27, as indicated in FIG. 2. Alternately, either the source-sensing unit and/or the output indicator unit may be separate from the electronics unit 24 and connected thereto by suitable external cable(s) 25, 27.

With reference to FIGS. 1 and 3, the train of infrared radiation pulses generated by source 10 under the control of pulse control 12 is diagrammatically indicated at 30 and the heartbeat modulated infrared radiation signal sensed by the sensor 14 is diagrammatically indicated at 32, the envelope of the signal being modulated due to reduced infrared radiation transmission corresponding to each systolic transition as indicated at points 34. The resulting signal from sensor 14 is passed by band pass amplifier 36 tuned to enhance the 2 Kilohertz signals, to attenuate signals above and below that frequency and to essentially completely block artifacts such as noise signals of frequency below 100 Hertz and transients above 4 Kilohertz. The output signal from amplifier 36 is applied to detector 38 to produce a fluctuating DC signal that contains the blood pulsing information. This fluctuating DC signal is applied to low pass filter 40 that is tuned to pass only signals of frequency well below the power distribution frequency (e.g. 60 Hertz) and then amplified by amplifier 42 which provides the output signal 44 which is applied to pulse generating circuit 46. That circuit is triggered in response to a pulse signal 44 and provides a square wave pulse 48 of fixed duration. Circuit 46 after being triggered cannot be triggered again for 0.3 second. At the end of that interval circuit 46 returns to a state where it can be triggered to produce another pulse 48. Output 48 is applied over line 50 to drive integrating meter 52 which is calibrated to display pulse rate directly. Other indicator devices such as visual indicator 54 or audible indicator 56 may also be employed to provide pulse rate indications.

A schematic diagram of the particular embodiment is shown in FIG. 4. Infrared radiation source 10 is connected via resistor 60 between positive terminal 58 and pulse control 12 in the form of multivibrator 62 that is connected to negative terminal 64. The components of multivibrator 62 are selected to provide an oscillation cycle of 2 Kilohertz frequency with a twenty percent ON time which produces a series of pulses 30 that produce a correspnding series of infrared radiation pulses. In this circuit, current flows through diode 10 for 0.1 millisecond every half millisecond. Resistor 60 limits the current flow to a peak of about 20 milliamperes.

The pulses 30 of infrared radiation energy from source 10 pass into the patient's flesh and are sensed by infrared radiation detector 14 which is used in photovoltaic mode and generates a pulse signal which is applied to the inverting terminal of operational amplifier 72 which has a feedback network of capacitor 74 and resistor 76. The output of amplifier 72 is coupled to amplifier 88 which has a feedback network of resistor 82 and capacitor 84. These two amplifier stages have a band pass characteristic of about 500 Hertz band width centered at 2 Kilohertz so that the 2 Kilohertz pulse train signal 32 is passed and artifacts below 100 Hertz (such as power distribution signals of 60 Hertz frequency) and higher frequency artifacts such as transients of frequency above about 4 Kilohertz are essentially excluded. The gain of this band pass amplifier at 2 Kilohertz is about 300 which raises the signal level to about 1 volt to the input of diode 92 in the detector circuit so that the forward drop of detector diode 92 is exceeded.

The output from diode 92 is a pulsing signal which is smoothed by a filter that includes capacitor 94 and resistor 96 and then is coupled by capacitor 98 to operational amplifier 100. The feedback circuit of that amplifier includes resistors 102 and 104 and capacitor 108 and has a time constant of about 1 second and that amplifier provides a low pass characteristic such that an output in the form of a pulse 44 as indicated in FIG. 3c corresponding to each heartbeat and having an amplitude of about 0.2 volts is produced. The next operational amplifier stage 114 has a gain of about 100 and saturates so that a shaped pulse signal corresponding to each pulse 44 is applied to comparator circuit 132 and then to a differentiator circuit that includes capacitor 140 and resistor 142 to generate a negative triggering spike.

Each triggering spike is applied to one-shot pulse generator 46 which produces a positive square wave pulse 48 as indicated in FIG. 3d of about 0.3 seconds duration which is applied to energize light emitting diode (visual indicator) 54. If switch 154 is in its lower position as indicated in FIG. 4, audible indicator 56 is connected in series with visual indicator 54, while indicator 56 is bypassed when switch 154 in its upper position.

The output from one-shot 46 is also applied through diode 158 and resistor 160 to voltage reference diode 162 which standardizes the output pulse of the multivibrator to an amplitude of 0.4 volts independent of the supply voltage. The resulting pulse which is standardized in both amplitude and duration is applied to the input of integrating amplifier 168 which supplies an output signal that is proportional to the patient's pulse rate. This output signal is displayed by meter 52. Diode 176 provides an offset so that the scale of the meter 52 does not respond to low pulse rates and thus that scale is calibrated only in terms of higher pulse rates, e.g. above 50 pulses per minute.

Suitable values for components in a particular embodiment of the circuitry shown in FIG. 4 are set out in the following table:

| Component | | Value or Type |
| --- | --- | --- |
| Infrared source | 10 | GE SSL55CF |
| Photodiode | 14 | Clairex CLT2160 |
| One-Shot | 46 | ½ Signetics 556 |
| Meter | 52 | LFE 4003 (0–1 milliamp) |
| Visual Indicator | 54 | Fairchild FP 110 |
| Audible Indicator | 56 | Mallory SNP 428 |
| Resistor | 60 | 100 Ohms |
| Multivibrator | 62 | ½ Signetics 556 |
| Resistor | 66 | 47 Kilohms |
| Resistor | 68 | 10 Kilohms |
| Capacitor | 70 | 0.1 microfarad |
| Operational Amplifier | 72 | ⅓ Siliconex L144 |
| Capacitor | 74 | 22 picofarads |
| Resistor | 76 | 5 Megohm |
| Resistor | 78 | 60 Kilohms |
| Resistor | 80 | 3.3 Kilohms |
| Resistor | 82 | 1.4 Kilohms |
| Capacitor | 84 | 0.01 microfarad |
| Capacitor | 86 | 0.01 microfarad |
| Operational Amplifier | 88 | ⅓ Siliconex L144 |
| Resistor | 90 | 10 Kilohm |
| Diode | 92 | 1 N 914 |
| Capacitor | 94 | 0.1 microfarad |
| Resistor | 96 | 1 Megohm |
| Capacitor | 98 | 0.1 microfarad |
| Amplifier | 100 | ⅓ Siliconex L144 |
| Resistor | 102 | 1 Megohm |
| Resistor | 104 | 1 Megohm |
| Resistor | 106 | 10 Kilohms |
| Capacitor | 108 | 0.1 microfarad |
| Resistor | 110 | 10 Kilohms |
| Capacitor | 112 | 0.1 microfarad |
| Amplifier | 114 | ⅓ Siliconex L144 |
| Resistor | 116 | 20 Megohms |
| Resistor | 118 | 1 Megohm |
| Resistor | 120 | 1 Megohm |
| Resistor | 122 | 1 Megohm |
| Resistor | 124 | 10 Kilohms |
| Resistor | 126 | 0.1 microfarad |
| Capacitor | 128 | 0.1 microfarad |
| Resistor | 130 | 1 Megohm |
| Amplifier | 132 | ⅓ Siliconex L144 |
| Resistor | 134 | 1 Megohm |
| Resistor | 136 | 1 Megohm |
| Resistor | 138 | 270 Kilohms |
| Capacitor | 140 | 0.1 microfarad |
| Resistor | 142 | 470 Kilohms |
| Resistor | 146 | 2.2 Megohms |
| Resistor | 148 | 1 Kilohm |
| Capacitor | 150 | 0.1 microfarad |
| Diode | 158 | 1 N 914 |
| Resistor | 160 | 10 Kilohms |
| Diode | 162 | 1 N 816 |
| Capacitor | 164 | 0.1 microfarad |
| Resistor | 166 | 22 Kilohms |
| Amplifier | 168 | ⅓ Siliconex L144 |
| Resistor | 170 | 13 Kilohms |
| Capacitor | 172 | 68 microfarads |
| Resistor | 174 | 100 Kilohms |
| Diode | 176 | 1 N 914 |
| Resistor | 178 | 1 Kilohm |
| Capacitor | 184 | 22 microfarads |
| Resistor | 186 | 300 Ohms |

While a particular embodiment of the invention has been shown and described, various modifications thereof will be apparent to those skilled in the art and therefore it is not intended that the invention be limited to the disclosed embodiment or to details thereof and departures may be made therefrom within the spirit and scope of the invention as defined in the claims.

What is claimed is:

1. Compact monitor apparatus for monitoring a blood circulation condition comprising:

a source of infrared radiation, infrared sensor means mounted in spaced, side by side relation to said infrared source, said source and said sensor means being arranged whereby, when applied to a skin surface said source and said sensor means are exposed to spaced but immediately adjacent skin surface areas, oscillator means for energizing said infrared source to generate a series of pulses of infrared radiation at a relatively high frequency that is substantially greater than the power distribution frequency, whereby the pulsating blood flow immediately beneath the skin surface area significantly changes the transmission of infrared radiation as a function of the amount of blood in that region and thus imposes a modulation at a relatively low frequency that is substantially less than said power distribution frequency on the amplitude of the relatively high frequency pulses of infrared radiation emanating from the skin surface as sensed by said sensor means, band pass circuitry means connected to said sensor means and tuned to pass only signals in a frequency band that has a lower limit greater than said power distribution frequency and an upper limit less than three times said relatively high frequency, detector circuitry means connected to said band pass circuitry means for producing a series of output pulses as a function of the modulated pulse signals passed by said band pass circuitry means, low pass circuitry means, connected to said detector circuitry means and tuned to pass only signals at a frequency substantially less than said power distribution frequency, such that the relatively low frequency components of the output pulses from said detector circuitry means are passed and the relatively high frequency pulse components of said output pulses are blocked, pulse generator means connected to said low pass circuitry means to generate a pulse of predetermined amplitude and duration in response to each output pulse from said low pass circuitry means, the repetition rate of said pulse generator being limited to a maximum rate of about three pulses per second, and output indicator means connected to respond to said pulses of predetermined amplitude and duration from said pulse generator means to produce an indication of the monitored blood circulation condition as a function of the modulation by said pulsating blood flow of the series of infrared radiation pulses as sensed by said infrared sensor.

2. The apparatus as claimed in claim 1 wherein said source and said sensor means are mounted in a housing, said housing having a surface adapted to contact the surface of the skin at the body location to be monitored and said source and said sensor means protruding from said surface to form indentations in the skin surface with which said surface is in contact.

3. The apparatus as claimed in claim 1 wherein said band pass circuitry means has a pass band of less than 1 Kilohertz centered at a frequency of at least about 1 Kilohertz.

4. The apparatus as claimed in claim 1 wherein the center frequency of said band pass circuitry means is substantially the same as the frequency of said oscillator means.

5. The apparatus as claimed in claim 1 wherein said radiation source and said radiation sensor means are each solid state devices.

6. The apparatus as claimed in claim 1 wherein the frequency of said oscillator means is in the audio range.

7. The apparatus as claimed in claim 1 wherein said source and said sensor means are spaced at a range of 0.1–1.0 inch apart.

8. The apparatus as claimed in claim 1 wherein said output indicator means includes integrating circuit means that produces an output signal level corresponding to the monitored blood circulation condition.

9. The apparatus as claimed in claim 1 wherein said source and said sensor means are mounted in a housing and protrude from the housing at least about 0.05 inch.

10. Compact monitor apparatus for monitoring a blood circulation condition comprising:
a radiation source,
and radiation sensor means mounted in spaced, side by side relation,
means for energizing said radiation source to generate radiation, whereby upon application of said source and said sensor means to skin of the human body,
the pulsating blood flow immediately beneath said skin surface area significantly changes the transmission of radiation as a function of the amount of blood in that region and thus modifies the radiation emanating from the skin surface as sensed by said sensor means to produce pulsating blood signals,
filter circuitry means connected to said sensor means and tuned to attenuate artifact signals and enhance said pulsating blood signals,
pulse generator means connected to said filter circuitry means to generate a pulse of predetermined amplitude and duration in response to each of said enhanced pulsating blood signals, the repetition rate of said pulse generator means being limited to a maximum rate of about three pulses per second,
and output indicator means connected to respond to said pulses or predetermined amplitude and duration to produce an indication of the monitored blood circulation condition as a function of the modulation by said pulsating blood flow of the radiation as sensed by said sensor.

11. Compact monitor apparatus for monitoring a blood circulation condition comprising a housing,
a radiation source,
and radiation sensor means mounted in spaced, side by side relation in said housing, said source and said sensor proruding from said housing and being arranged so that in use when applied to the skin said source and said sensor means form spaced but immediately adjacent indentations in the skin surface area to which the housing is in contact,
means for energizing said radiation source to generate radiation,
whereby the pulsating blood flow immediately beneath said skin surface area significantly changes the transmission of radiation as a function of the amount of blood in that region and thus modifies the radiation emanating from the skin surface as sensed by said sensor means generating pulsating blood signals,
filter circuitry means connected to said sensor means and tuned to attenuate artifact signals and enhance said pulsating blood signals,
and output indicator means connected to respond to said enhanced pulsating blood signals to produce an indication of the monitored blood circulation condition as a function of the modulation by said pulsating blood flow imposed on the radiation as sensed by said sensor means.

12. The apparatus as claimed in claim 11 wherein said radiation source and said radiation sensor means are each solid state devices.

13. The apparatus as claimed in claim 12 wherein said source and said sensor means are spaced at a range of 0.1–1.0 inch apart.

14. The apparatus as claimed in claim 13 wherein said source and said sensor means protrude from said housing at least about 0.05 inch.

15. The apparatus as claimed in claim 14 and further including oscillator means for energizing said source to generate a series of pulses of radiation and wherein said filter circuitry means includes band pass circuitry means that has a pass band of less than one Kilohertz centered at a frequency that is substantially the same as the frequency of said oscillator means.

16. The apparatus as claimed in claim 15 and further including pulse generator means connected to said filter circuitry means to generate a pulse of predetermined amplitude and duration in response to each enhanced pulsating blood signals produced by said filter circuitry means, the repetition rate of said pulse generator means being limited to a maximum rate of about three pulses per second.

17. The apparatus as claimed in claim 16 wherein said output indicator means includes integrating circuit means that produces an output signal level corresponding to the monitored blood circulation condition.

18. The apparatus as claimed in claim 17 wherein the output of said source is in the infrared region and said sensor means is responsive to infrared radiation.

* * * * *